United States Patent [19]
Dixon et al.

[11] Patent Number: 6,033,680
[45] Date of Patent: *Mar. 7, 2000

[54] SHELF STABLE SKIN CLEANSING LIQUID WITH GEL FORMING POLYMER AND LIPID

[75] Inventors: Thomas Jefferson Dixon, Cincinnati, Ohio; Robert Raymond Schmidt, Fort Wright, Ky.; Mark Leslie Kacher, Mason, Ohio; Constance Sagel Koczwara, Milford, Ohio; Fernando Ray Tolléns, Cincinnati, Ohio; Marcus Wayne Evans, Hamilton, Ohio; Nicholas William Geary, Blue Ash, Ohio

[73] Assignee: The Procter & Gamble Company, Cincinnati, Ohio

[*] Notice: This patent is subject to a terminal disclaimer.

[21] Appl. No.: 09/116,074

[22] Filed: Jul. 15, 1998

Related U.S. Application Data

[63] Continuation of application No. 08/739,490, Oct. 28, 1996, Pat. No. 5,869,070, which is a continuation of application No. 08/349,773, Dec. 6, 1994, abandoned.

[51] Int. Cl.[7] ...................................................... A61K 7/48
[52] U.S. Cl. ........................ 424/401; 424/78.02; 514/844; 514/845; 514/846
[58] Field of Search ................................ 424/401, 78.02; 514/844, 845, 846

[56] References Cited

U.S. PATENT DOCUMENTS

| | | | |
|---|---|---|---|
| 5,312,559 | 5/1994 | Kacher et al. | 252/125 |
| 5,869,070 | 2/1999 | Dixon et al. | 424/401 |

*Primary Examiner*—Jyothsna Venkat
*Attorney, Agent, or Firm*—Darryl C. Little

[57] ABSTRACT

The liquid composition is a dual cleanser and moisturizer that is stable and on a macro scale is homogeneous. The dual cleansing and lipid moisturizing liquid composition of this invention comprises: by weight parts of the liquid composition:

(a) from about 5 parts to about 30 parts of lipid skin moisturizing agent having a Vaughan Solubility Parameter (VSP) of between 5 and 10;

(b) from about 0.3 parts to 5 parts of a water dispersible gel forming polymer wherein said polymer is an anionic, nonionic, cationic or hydrophobically modified polymers, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixes thereof; and, (c) from about 5 part to about 30 parts of a synthetic surfactant;

(d) from about 0 part to about 15 part of a C8 to C14 fatty acid soap; wherein said soap has a counterion selected from the group consisting of: K, NH4, N(CH2CH20H) 3; and mixtures thereof; and (e) water; and, wherein said lathering skin cleansing liquid composition has a Lipid Deposition Value (LDV) of at least 5 up to about 1000 $\mu$g of lipid per sq. cm of skin; and wherein said synthetic surfactant and said soap has a combined CMC equilibrium surface tension value of from 15 to 50.

This composition provides good cleansing, lather and good sensory feel and yet surprisingly provides a lipid moisturizing benefit via deposition of the lipid on the skin of the user. The liquid composition is stable and on a macro scale is homogeneous.

17 Claims, No Drawings

SHELF STABLE SKIN CLEANSING LIQUID WITH GEL FORMING POLYMER AND LIPID

CROSS-REFERENCE TO RELATED APPLICATIONS

This application is a continuation of application Ser. No. 08/739,490, filed Oct. 28, 1996, which application is issued as U.S. Pat. No. 5,869,070, which is a continuation of application Ser. No. 08/349,773, filed Dec. 6, 1994, now abandoned.

TECHNICAL FIELD

The present invention relates to personal skin moisturizing and cleansing compositions.

BACKGROUND OF THE INVENTION

Moisturizers are usually applied directly to the skin as leave-on products. Personal cleansing products are usually applied with water as a foam or lather and rinsed off with clear water. Ideal rinse off personal cleansers should cleanse the skin gently, causing little or no irritation without defatting and or drying the skin and without leaving skin taut after frequent use. Most lathering personal cleansing products, bar soaps, liquids and syndet liquids fail in this respect.

Some current commercial personal cleansing liquids claim to "moisturize" the skin. But, most of these current cleansing liquid products do not deliver an adequate moisturizing benefit. Therefore, users typically must moisturize their skin with a separate leave-on product following cleansing.

It would be highly desirable to improve the delivery of skin moisturizers from a cleansing liquid composition over the current commercial personal cleansing liquids. If this were accomplished it would provide users with the convenience of obtaining both a cleansing and a moisturizing benefit from a single product.

Dual cleansing and lipid moisturizing liquid compositions are very difficult to formulate and process. One reason is the cleansing ingredients, in general, tend to be incompatible with the lipid moisturizing ingredients. Another problem is processing on a commercial scale. Yet another problem is getting the lipid in the liquid to deposit on the skin of the user. The deposition of lipid moisturizer from the liquid, onto the skin can be very low due to loss of the lipid in the wash and the rinse. Conversely, it can feel too sticky if deposited on the skin. Still another problem is formulating a dual liquid that lathers well. Another problem is formulating a dual liquid that is storage stable.

The actual deposition of lipid moisturizer from a lathering dual liquid composition is essential for effective lipid benefit. No known commercial prior art liquid that claims to be a cleansing and lipid moisturizing liquid, deposits as much 3 micrograms of lipid moisturizer per cm. sq. of washed skin.

U.S. Pat. No. 3,829,563, Barry et al., issued Aug. 13, 1974, discloses an emollient cleansing composition containing 10–70% by weight petrolatum with up to 98%, preferably, 95–98%, having a diameter particle size smaller than 5 microns.

U.S. Pat. No. 5,308,526, Dias et.al., issued May 3, 1994, incorporated herein by reference, discloses liquid skin compositions with up to 5 parts petrolatum wherein 20–80% of said petrolatum particles have a particle size from 10–120 microns.

U.S. Pat. No. 5,312,559, Kacher et al., issued May 17, 1994, incorporated herein by reference, discloses semi-solid compositions of 60,000 to 400,00 cps containing 0.5 parts to 15 parts petrolatum having a particle size distribution in which 20% to 80% of the particles are 10–120 microns.

It is an object of the present invention to provide an effective, yet gentle, dual skin cleansing liquid composition which actually deposit enough lipid on the skin to provide superior skin moisturizing and sensory benefits while maintaining its lathering and cleaning properties.

SUMMARY OF THE INVENTION

The liquid of the present invention is a shelf stable lathering skin cleansing liquid composition comprising by weight parts of the liquid composition:

(a) from about 5 parts to about 30 parts of lipid skin moisturizing agent having a Vaughan Solubility Parameter (VSP) of between 5 and 10;

(b) from about 0.3 parts to 5 parts of a water dispersible gel forming polymer wherein said polymer is an anionic, nonionic, cationic or hydrophobically modified polymers, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixes thereof; and, (c) from about 5 part to about 30 parts of a synthetic surfactant;

(d) from about 0 part to about 15 part of a C8 to C14 fatty acid soap; wherein said soap has a counterion selected from the group consisting of: K, NH4, N(CH2CH2OH)3; and mixtures thereof, and (e) water; and, Wherein said lathering skin cleansing liquid composition has a Lipid Deposition Value (LDV) of at least 5 up to about 1000; and Wherein said synthetic surfactant and said soap has a combined CMC equilibrium surface tension value of from 15 to 50.

The liquid composition is stable and on a macro scale is homogeneous.

DETAILED DESCRIPTION OF THE INVENTION

The present invention can provide a dual cleansing and lipid moisturizing liquid composition: 1) which produces an abundant, stable, high quality lather, 2) which is an effective skin cleanser, 3) which is very mild to the skin and ocular mucosae, 4) which actually delivers an effective amount of a lipid moisturizing agent to the skin of the user during the wash; 5) which is non-sticky after use, and 6) which is storage stable.

The present liquid is a lathering skin cleansing liquid composition comprising by weight parts of the liquid composition:

(a) from about 5 parts to about 30 parts of lipid skin moisturizing agent having a Vaughan Solubility Parameter (VSP) of between 5 and 10;

(b) from about 0.3 parts to 5 parts of a water dispersible gel forming polymer wherein said polymer is an anionic, nonionic, cationic or hydrophobically modified polymers, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixes thereof; and, (c) from about 5 part to about 30 parts of a synthetic surfactant;

(d) from about 0 part to about 15 part of a C8 to C14 fatty acid soap; wherein said soap has a counterion selected from the group consisting of: K, NH4, N(CH2CH2OH)3; and mixtures thereof; and (e) water; and, Wherein said lathering skin cleansing liquid composition has a Lipid Deposition Value (LDV) of at least 5 up to about 1000; and Wherein said synthetic surfactant and said soap has a combined CMC equilibrium surface tension value of from 15 to 50.

GLOSSARY OF TERMS

The term "Oil in Water Emulsion Stabilizer" as used herein, is defined as an ingredient that helps to prevents the oil or lipid from separating in a cleanser's neat form while allowing lipid to be released to deposit on the skin wend used in bath or shower, some examples of such stabilizers are: crystalline ethylene glycol fatty acid ester, water dispersible gel forming polymer or a combination of this ester and a water dispersible gel forming polymer.

The term "Shelf Stable Liquid Cleanser," as used herein, is defined as a neat lathering skin cleansing liquid composition that under ambient conditions does not phase separate for at least two weeks, preferably for at least six months, and more preferable never.

The term "Lipid Release", as used herein, means that a lipid in a liquid emulsion cleanser will release or separate from the emulsion upon dilution to lather concentrations. Such a liquid cleanser will provide improved lipid deposition.

The term "Water Dispersible Gel Forming Polymer" as used herein means that the polymer is water dispersible and forms a gel in water of the liquid cleanser at 5 to 40° C.

Vaughan Solubility Parameter (VSP) is a calculated parameter used to define a lipid's solubility. Vaughan parameters typically have a range of 5–25.

Lipid Deposition Value (LDV) is a measure of how much lipid is deposited on skin from compositions herein, the reading corresponds to the amount measured using a Sebumeter (typically the mean of four-six readings), as defined in Lipid Deposition Protocol 1, herein.

Equilibrium Surface Tension is a measure of surface tension of a surfactant as measured at the critical micelle concentration at 25° C.; units are dynes/cm.

Consistency, k, is a measure of lipid viscosity, used in combination with Shear index, to define viscosity for materials whose viscosity is a function of shear. The measurements are made at 35° C. and the units are poise (equal to 100 cps).

Shear index, n, is a measure of lipid viscosity, used in combination with Consistency, to define viscosity for materials whose viscosity is a function of shear. The measurements are made at 35° C. and the units are dimensionless.

Elastic Modulus G' is used to define rheological properties of lipid and is a measurement of a lipids ability to store or return energy. The measurements are made at 35° C. and the units are dynes/sq. cm.

Viscous Modulus G" is used to define rheological properties of lipid and is a measurement of unrecoverable energy. The measurements are made at 35° C. and the units are dynes/sq. cm.

All parts, percentages and ratios used herein are by weight basis and all measurements are at 25° C., unless otherwise indicated.

THE WATER DISPERSIBLE GEL FORMING POLYMER

The oil in water stabilizer is a water dispersible gel forming polymer. This stabilizer is not a self lathering surfactant. This polymer is preferably an anionic, nonionic, cationic or hydrophobically modified polymers. This polymer is selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixes thereof. Preferably, the polymer is selected from the group consisting of Sodium Polyacrylate, Hydroxy Ethyl Cellulose, Cetyl Hydroxy Ethyl Cellulose, and Polyquaternium 10.

Liquid cleanser compositions that contain the water dispersible gel forming polymer do not require ethylene glycol fatty acid ester. Such compositions have from 0.3 parts to 5 parts, more preferably 0.8 parts to 3 parts, water dispersible gel forming polymer. In the product that contains no ethylene glycol fatty acid esters, 0.3 parts to 3 parts water dispersible gel forming polymer, preferably chosen from the group consisting of Sodium Polyacrylate, Hydroxy Ethyl Cellulose, Cetyl Hydroxy Ethyl Cellulose, and Polyquaternium 10, and from 0.5 parts to 6 parts from the group consisting of C10–C18 fatty alcohol, oleyl alcohol, C10–C18 fatty acid, and oleyl acid, and mixtures thereof. Most preferably, these liquid compositions contain from 1.0 parts to 5.0 parts selected from C16, C18, and Oleyl alcohol, or myristic acid; and mixtures thereof.

The water dispersible gel forming polymer can also improve the sensory feel of the lipid on skin in addition to product stabilization. The improved sensory results from reduced tackiness and greasiness and improved smoothness. It is an especially preferred embodiment to use mixture of polymers, some of which are preferred for product stabilization, some are preferred for improved sensory. Preferred polymers to improve sensory are selected from the following group consisting: of polyethylene glycol, hydroxypropyl guar, guar hydroxypropyltrimonium chloride, polyquaternary 3, 5, 6, 7, 10, 11 and 24 and mixes thereof.

Polymers that do not form gels with water are optional and are not used by themselves or to stabilize the liquid composition of this invention.

The above selected oil in water stabilizer of present invention can be used in combination with other oil in water stabilizers. But is preferably used by itself in the context of this invention.

This stabilizer provides improved shelf stability but allows the lipid in water emulsion to separate upon dilution to a lather concentration and thereby provide for increased lipid deposition onto the skin.

Another optional non-surfactant oil in water emulsification stabilizer is crystalline C10–C22 ethylene glycol fatty acid ester. The ethylene glycol fatty acid ester can comprise from 1 part to 15 parts, preferably from 1 part to 10 parts, more preferably from 3 parts to about 8 parts of the liquid. The ester is preferably a diester, more preferably C14–C18 diester, most preferably, Ethylene Glycol Distearate. While not being bound by theory, it is believed that the ester form an insoluble particle network, preferably platelet crystals, that prevent the coalescence of lipid particles, thus preventing phase separation of the product. This network breaks down on dilution in the lather, resulting in emulsion instability in the lather and deposition of lipid on skin. In these compositions from 1 parts to 15 parts C10–C22 ethylene glycol fatty acid esters and 0.0.05 parts to 3 or 5 parts , more preferably 0.3 parts to 3 parts, of polymer gel former is used.

Some preferred compositions that are free of the above ester have better lather than those with the ester.

LIPID RELEASE TEST

The following test is used to determine whether or not some lipid in a lipid in water liquid cleanser product will be "released" or separate as a lipid phase.

A twenty percent (20%) solution of the neat liquid cleanser is made by weighing 5 grams of neat liquid product into a 100 ml beaker and adding 20 grams of 75–78 F. (22–24 C.) tap water of hardness 7–8. It is stirred for 3 minutes on a magnetic stirplate with a 1 ½" (3.75 cm.) stir bar at a medium setting with a good vortex.

The stirred sample is poured into a graduated cylinder (preferably 10 ml) and observed for 1 Hour at room temperature. Preferred compositions show phase separation during this time period, with a clear layer at or near the bottom, indicative of the lighter lipid phase separating to the top. Less preferred compositions take longer to separate.

No known commercially available prior art liquid cleanser that contains a lipid has a measurable separation during the 1 hour period, when subjected to the above test. While not being bound to any theory, the probable reason for this is that those prior art liquids are over emulsified with surfactant and/or non-crystalline emulsifiers.

THE LIPID SKIN MOISTURIZING AGENT

The lipid skin moisturizing agent in the liquid composition provides the skin of the user with a moisturization benefit via deposition of the lipid on skin during use. In this invention the lipid skin moisturizing agent is defined with scrutiny. The lipid type and its physical properties in this present invention hold the key to the overall product effectiveness, and is restricted to a hydrophobic material with the following defined physical and rheological properties.

VAUGHAN SOLUBILITY PARAMETER VALUE (VSP)

The lipid in this present invention is further defined by its solubility parameter, as defined by *Vaughan in Cosmetics and Toiletries,* Vol. 103, p47–69, October 1988. A lipid having a Vaughan Solubility Parameter Value (VSP) of from 5 to 10, preferably 5.5 to 9, more preferably where at least 70% of said lipid has a VSP of 6.5 to 7.75 for use in the liquid compositions herein.

| VAUGHAN SOLUBILITY PARAMETER TABLE* | |
|---|---|
| Cyclomethicone | 5.92 |
| Squalene | 6.03 |
| Mineral Oil | 7.09 |
| Petrolatum | 7.33 |
| Isopropyl Palmitate | 7.78 |
| Isopropyl Myristate | 8.02 |
| Castor Oil | 8.90 |
| Cholesterol | 9.55 |

*As reported in Solubility, Effects in Product, Package, Penetration and Preservation, C. D. Vaughan, Cosmetics and Toiletries, Vol. 103, October 1988.

Fatty acids, fatty acid soaps and water soluble polyols are specifically excluded from our definition of a lipid. Thus stearic acid, glycerine and propylene glycol are excluded from our definition of a lipid.

SOME PREFERRED LIPIDS

Notwithstanding the rheological and solubility requirements, a wide variety of lipid type materials and mixtures of materials are suitable for use in the compositions of the present invention. Preferably, the lipid is selected from the group consisting of hydrocarbons oils and waxes, silicones, fatty acid derivatives, cholesterol, cholesterol derivatives, di and tri-glycerides, vegetable oils, vegetable oil derivatives, and acetoglyceride esters, alkyl esters, alkenyl esters, lanolin and its derivatives, milk -tri-glycerides, wax esters, beeswax derivatives, sterols and phospholipids mixtures thereof.

Hydrocarbon oils and waxes: Some examples are petrolatum, mineral oil micro-crystalline waxes, polyalkenes, paraffins, cerasin, ozokerite, polyethylene and perhydrosqualene.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

Milk glycerides are useful and an example is hydroxylated milk glyceride.

Polyol fatty acid polyesters are also useful.

Wax esters, such as beeswax and beeswax derivatives, spermaceti, myristyl myristate, stearyl stearate are also useful. Vegetable waxes are useful and some examples are carnauba and candelilla waxes. Sterols are useful and some examples are cholesterol, cholesterol fatty acid esters. Phospholipids, such as lecithin and derivatives, Sphingo lipids, ceramides, glycosphingo lipids are also useful.

It is more preferred when at least 70% of the lipid is selected from the group consisting: petrolatum, mineral oil micro-crystalline waxes, paraffins, ozokerite, polyethylene, hydrogenated polybutene, polydecene and perhydrosqualene. dimethicones, cyclomethicones, alkyl siloxanes, polymethylsiloxanes and methylphenylpolysiloxanes, and mixture thereof.

It is most preferred when at least 75% of lipid is composed of lipids selected from the group consisting: petrolatum, mineral oil, hydrogenated polybutene, and polydecene, and mixtures thereof, and wherein the ratio of petrolatum to the other selected lipids (hydrogenated polybutene or polydecene or mineral oil) is from about 10:1 to about 1:3, more preferably from about 5:1 to about 1:1.

The lipid is preferably in the liquid as an emulsion having droplets ranging from about 0.1 microns to 100 microns, excluding anomalous very small or a few very large particles. Preferably greater than 25% of the lipid particles are front 5 microns to 120microns and more preferably at least 40% of the lipid particles are from about 5 microns to 20 microns. An especially preferred particle size range is from 15% to 35% of particles having a particle size of 0.1 to 5 micron, 15 to 45% having a particle size of between 5 and 10 microns, from 30% to 50% having a particle size between 10 and 15 micron, and less than 15% having a particle size greater than 15 micron. It is a surprising aspect that high levels of large particle lipid can be stable in a liquid cleansing composition and also deposit efficacious levels in the washing process. While not being bound by theory, larger particles typically deposit more efficiently than smaller particles.

While not being bound by any theory, lipids outside of the rheology properties defined herein below are either too easily emulsified and hence will not deposit, or are too "stiff" to adhere or deposit on to skin and provide a moisturization benefit. The lipid rheological properties are considered to have an important effect on lipid deposition. In addition, the rheological properties of the lipid are also important to user perception. Some lipids, on deposition to the skin, are considered too sticky and are not preferred by the user.

Lipid Rheological Table 1

| Range | k poise (1/sec)n-1 | n (dimensionless) | G' at 1 Hz (dynes/cm2) | G" at 1 Hz (dynes/cm2) |
|---|---|---|---|---|
| Most preferred | 50–2,000 | 0.20–.5 | 5,000–50,000 | 5,000-100,000 |
| More Preferred | 10–3,000 | 0.1–0.5 | 1,000–80,000 | 500-300,000 |
| Preferred | 5–5000 | 0.1–0.9 | 25–100,000 | 25-500,000 |

Two types of rheological parameters are used to define the lipid used herein. The viscosity of the fluid is represented by consistency (k) and shear index (n) and, while not being bound by any theory, is believed to represent the stickiness. The other type of parameter used herein, are the elastic modulus (G') and the viscous modulus (G"). While not being bound by any theory it is believed G' and G" are important factors determining the lipid's emulsification characteristics.

The useful lipid herein has a shear index, n, of from about 0.1 to about 0.8 and a consistency, k, of: from 5 to 5,000 poise; preferably 10 to 3000 poise; more preferably 50 to 2,000 poise at 35° C. The preferred lipid rheology is further defined in the following table:

The shear index, n, and consistency, k, are well accepted industry standards for reporting the viscosity profile of a material that has a viscosity that is a function of the shear rate.

For all materials the viscosity, which is defined for instance in "Chemical Engineering, by Coulson and Richardson" is given by:

$$\text{Viscosity}, \mu = \sigma/\gamma'$$

Where $\sigma$ is the shear stress, and $\sigma$ is the shear rate.

The viscosity for all materials is measured by either applying a shear rate and measuring the resultant shear stress or vice versa.

The Carrimed CSL 100 Controlled Stress Rheometer is used to determine Shear Index, n, and Consistency, k, for the lipids herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10-4 rad/sec, then this rate of strain is reported as a shear rate. These data are used to create a viscosity $\mu$ Vs. shear rate $\gamma$ flow curve for the material. This flow curve can then be modeled in order to provide a mathematical expression that describes the material's behavior within specific limits of shear stress and shear rate. These results were fitted with the following well accepted power law model (see for instance: *Chemical Engineering*, by Coulson and Richardson, Pergamon, 1982 or *Transport Phenomena* by Bird, Stewart and Lightfoot, Wiley, 1960):

$$\text{Viscosity}, \mu = k(\gamma')^{n-1}$$

Lipid Rheological Table 2

| Lipids | Consistency, k | shear index | G' at 1 HZ | G" at 1 Hz |
|---|---|---|---|---|
| Units | poise | n | dynes/sq. cm | dynes/sq. cm |
| Water | 0.01 | 1.0 | | |

-continued

Lipid Rheological Table 2

| Lipids | Consistency, k | shear index | G' at 1 HZ | G" at 1 Hz |
|---|---|---|---|---|
| Microcrystalline Wax (MC) | ** | ** | ** | ** |
| 80% Pet/20% MC wax | 3926–4822* | 0.31–33* | 306,400–621,000* | 434,000–594,580* |
| 91% Pet/9% MC Wax | 1983 | 0.15 | | |
| Petrolatum | 1080–1345 | 0.24 | 25,000–40,000 | 23,400–36,400 |
| 90% Pet/10% min oil | 767–780 | 0.26 | | |
| 80% Pet/20% min oil | 354–430 | 0.29–0.34 | 8,500–9300 | 6,700–7000 |
| 60% Pet/40% min oil | 111–115 | 0.42 | 1,000–2800 | 940–2500 |
| 40% Pet/60% min oil | 4.8–5.3 | 0.87 | 230–380 | 280 |
| Mineral (min) oil | 0.81–0.82 | 1.0 | | |
| 5%SE†/95% min oil | 1580–1787 | 0.16 | | |
| 95.9%SBO/4.1%MC wax | 780–890 | 0.13–0.16 | | |
| 80%Pet/20% Polydecene | 283–292 | 0.32–0.34 | 5881–7160 | 6118–6805 |
| 65%Pet/35% Polydecene | 115–120 | 0.4 | 1280–1407 | 1416–1446 |
| 20% Pet/80% Polydecene | 0.83 | 0.97–1.0 | 24.1 | 34.5 |
| 20% SE†/80% Polydecene | 1897–2035 | 0.19–0.22 | 1E6–1,370,000 | 280,000–980,000 |
| 80% Pet/20% Hydrogenated polybutene | 140–585 | 0.24–0.25 | | |

*Measured with same instrument, but with 2 cm parallel plate geometry.
**Too stiff and solid to obtain readings
†SE solid is a sucrose ester solid and is an example of a preferred polyol fatty acid polyester, SBO is soybean oil an Pet is petrolatum.

Note that mineral oil, microcrystalline wax and some other lipids by themselves have rheological properties that are unsuitable for use in the present liquid compositions; but may be blended with other lipids to provide acceptable lipid blends.

TEST PROTOCOL FOR DETERMINATION OF G' and G"

The Carrimed CSL 100 Controlled Stress Rheometer is used to perform oscillatory tests at 35° C. with the 4 cm 2° cone measuring system typically set with a 51 micron gap. The oscillatory tests at 35° C. are carried out in 2 steps. The first step is a stress amplitude sweep at the expected starting and ending frequencies for the frequency sweep. These tests allow a determination to be made as to whether or not the test conditions are within the linear viscoelastic region for the test material over the anticipated frequency range. The linear viscoelastic region is a region where there is a linear relationship between stress and strain. The second step is a frequency sweep made at a stress level within that linear viscoelastic region. The frequency sweep allows the test material's viscoelastic behavior to be measured. The oscillatory test on a controlled stress rheometer is performed by applying a stress in an oscillatory manner and measuring the resulting oscillatory strain response and the phase shift between the applied stress wave form and the resulting strain wave form in the test material. The resulting complex modulus is expressed as a combination of the material's elastic (G') and viscous (G") components:

The elastic modulus G' is a measure of a materials ability to store recoverable energy. This energy storage can be the result of the ability of a complex polymer, structural network, or a combination of these to recover stored energy after a deformation. The viscous or loss modulus G" is a measure of the unrecoverable energy which has been lost due to viscous flow.

The lipid is present in the liquid at a level of from about 5 parts to about 30 parts by weight of the liquid. Its more preferred levels are 10 parts to 25 parts.

Known market liquids that contain lipid deposit lipid at an efficiency of less than 3 microgram per sq. cm. of skin as measured by Deposition Protocol 1.

The lipid in this present invention is deposited on skin during use at an efficiency that produces at least 5 μg of lipid per sq. cm of skin. The preferred level of deposition is from about 10 μg/sq. cm to about 500 μg/sq. cm. The more preferred levels are from 15 or 25 μg/sq. cm to about 200 μg/sq. cm, as measured by lipid Deposition Protocol 1. It has been found that a certain minimum level of lipid is required in order to get any measurable deposition of the lipid on skin. While not being bound by theory, known market liquids that contain liquid almost exclusively rely on emulsification of lipid by surfactant to provide product stability of the resultant emulsion. However, this also results in stability of the emulsion when the product is diluted to form the lather, resulting in very poor deposition efficiency. It is an aspect of the current invention that the emulsion is stabilized in the product by non-surfactant means as well. The resultant emulsion tends to phase separate in the lather, resulting in excellent deposition of lipid on the skin.

LIPID DEPOSITION VALUE

The level of lipid deposition on skin can be measured by different protocols, all are modeled after how skin cleansing products are typically used by consumers. All the protocols are "in vivo", and all tests are made using a statistically designed protocol using at least 6 subjects per prototype.

All protocols consist of a common product application stage followed by a determination of the deposited lipid amount. The following two protocols only differ in the analytical technique used to quantify the amount of deposited lipid on the skin. The quantification of lipid is "in vivo" and as such has a wide variance due to differences in skin type and condition. To offset this a balanced design is used to test prototypes; balanced in skin type and using a large base size. In all cases product application and measurement is undertaken by a trained technician to reduce variability.

PREP FOR LIPID DEPOSITION FOR PROTOCOLS 1 & 2

The subject wets the entire surface of the inner forearm with 95–100° F. tap water. The technician, using an implement known as a "puff", applies 1 ml of product to the pre-wet pouf. The technician then rubs the pouf with a constant pressure and speed for 30 seconds (i.e., exactly 30 rubs up and 30 rubs down). The lather is allowed to remain on the forearm for fifteen seconds, followed by a thorough rinse for fifteen seconds with the water flowing from inner elbow to wrist. The subject arm is then pat dried with a paper towel. The subject then waves the arm to "air" dry for 30 seconds.

LIPID DEPOSITION PROTOCOL 1

The unit used is a Sebumeter SM810 which is commercially available from Courage and Khazaka GmbH and is reported to be recognized by the scientific world. The Sebumeter measures lipid on the skin via photometry of a special plastic strip, which becomes transparent when it absorbs lipids. The plastic strip is extended over a mirror which is connected to a spring. The measuring head of the device (comprised of spring, mirror and plastic strip) is pressed against the skin for 30 seconds. The value ($\mu$g/sq. cm) is indicative of the amount of lipid on the skin, and increases with increased amount of lipid. The method is insensitive to humidity. Sebumeter readings (4–6) are taken along the length of the forearm and the Lipid Deposition Value, LDV, ($\mu$g/sq. cm) is defined as the mean of the 4–6 readings, divided by 0.56 for petrolatum containing lipid mixtures. The 0.56 value is a conversion factor to translate sebumeter readings with petrolatum containing lipids to actual deposition levels in $\mu$g/sq. cm. Lipid deposition values of from 15 to 200 ug/sq. cm., more preferably from 30 to 150 ug/sq. cm. are preferred.

The Sebumeter has the following limitations:
1. The Sebumeter tape also detects natural skin lipids. A criterion of this test was that subjects baseline value measured on the Sebumeter, prior to washing, be less than or equal to 1 or 2 $\mu$g/sq. cm of forearm skin.
2. The Sebumeter like other surface extraction measurements may not measure all the deposited lipid, if the skin topography is undulating it is possible that deposited lipid may not be extracted by the Sebumeter tape.
3. The Sebumeter tape becomes saturated at a LDV of above about 300 $\mu$g/sq. cm; so it is understood that for deposition values above 300 $\mu$g/sq. cm, Protocol 2 is used.
4. Different lipid systems will have different conversion factors. For testing non-petrolatum lipids, a new calibration curve is required.

LIPID DEPOSITION PROTOCOL 2

The second protocol uses a solvent extraction method similar in type to that described in the *Journal Society of Cosmetic Chemists of Great Britain* Vol. 21 (p 521–532), 1970. An extraction cup is firmly attached to the forearm and heptane poured in to the cup, such that it is in contact with the forearm. The solvent extract containing the extracted lipid is analyzed by standard gas chromatographic methods.

THE LATHERING SYNTHETIC SURFACTANT

The liquid composition comprises a lathering synthetic surfactant selected from the group consisting of anionic surfactants; nonionic surfactants, cationic surfactants, amphoteric surfactants, and mixtures thereof.

The lathering synthetic surfactant is defined herein as a synthetic surfactant or mixes thereof that when combined have an equilibrium surface tension of between 15 and 50 dynes/cm, more preferably between 25 and 40 dynes/cm as measured at the CMC (critical micelle concentration) at 25° C. Some surfactant mixes can have a surface tension lower than those of its individual components.

TABLE OF SOME SYNTHETIC SURFACTANTS SURFACE TENSION*

| Surfactant | Surface tension at CMC (dynes/cm) |
|---|---|
| Anionics | |
| Sodium Dodecane Sulfonate | 43 |
| Potassium Dodecane Sulfonate | 38 |
| Sodium Dodecyl Sulfate | 40 |
| Sodium Tetradecyl Sulfate | 35 |
| Sodium hexadecyl Sulfate | 37 |
| Sodium Dodeceth-2 Sulfate | 42 |
| Sodium Decyl Benzene Sulfonate | 48 |
| Sodium Dodecyl Benzene Sulfonate | 47 |
| Sodium Hexadecyl Benzene Sulfonate | 45 |
| Cationics | |
| Tetradecyl Trimethyl Ammonium Bromide | 41 |
| Dodecyl Trimethyl Ammonium Methane Sulfonate | 39 |
| Zwitterionics | |
| Dodecyl Betaine | 33 |
| Hexadecyl Betaine | 35 |
| Dodecyl Benzyl methyl Ampho Acetate | 33 |
| Nonionics | |
| 1,2 Dodecyldiol | 23 |
| 1,3 Pentadecyldiol | 27 |
| Hexeth-6 | 32 |
| Deceth-6 | 30 |
| Dodeceth-3 | 28 |
| Dodeceth-12 | 40 |
| Hexadeceth-6 | 32 |
| Hexadeceth-21 | 45 |
| Nonoxynol-10 | 31 |
| Nonoxynol-30 | 41 |
| Dimethicone copolyol | 21–22 |

*As calculated from Surfactants and Interfacial Phenomena by Rosen, Wiley, 1988)

TABLE OF SOME PREFERRED SURFACTANTS SURFACE TENSION**

| Surfactant | Surface tension (dynes/cm) |
|---|---|
| C12–C14 Glycerylether sulfonate | 47 |
| Sodium Lauryl Isethionate | 42 |
| Sodium Coco Isethionate | 42 |
| Sodium Stearyl Isethionate | 72 |
| Sodium Ether (3) Sulphate | 47 |
| Sodium Coco Taurate | 43 |
| Sodium Lauryl Sarcosinate | 42 |

**Measured on Kruss BP-10 Dynamic surface tensiometer, these measurements were not equilibrium, nor at the CMC. Equilibrium measurements are typically lower than Dynamic.

The combined personal cleansing and moisturizing liquid composition herein comprises at least from about 5 part to about 30 parts, preferably from about 5 parts to about 25 parts, and most preferably from about 10 parts to about 25 parts of a lathering synthetic surfactant.

Anionic surfactants useful herein include: acyl isethionates, acyl sarcosinates, alkylglycerylether sulfonates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphates, the alkyl ether sulfates (with 1 to 12 ethoxy groups), and mixtures thereof, wherein said surfactants contain C8 to C22 alkyl chains and wherein the counterion is selected from the group consisting of: Na, K, $NH_4$, $N(CH_2CH_2OH)_3$. The anionic surfactant is more preferred when selected from the group consisting of acyl isethionate, acyl sarcosinates, acyl lactylates, alkyl sulfosuccinates, alkylglyceryl ether sulfonates, methylacyl taurates, alkyl ether sulfates, alkyl sulfates, alkyl phosphate esters and mixtures thereof, wherein said surfactants contain has C8 to C14 alkyl chains and is present at a level of from about 8 to about 15 parts;

Amphoteric synthetic surfactants cannot serve as the sole surfactant in this product, but are preferred as a co-surfactant at a lower level of from about 1 part to about 10 parts, by weight and the more preferred types are selected from alkyl-ampho mono- and di-acetates, alkyl betaines, alkyl dimethyl amine oxides, alkyl sultaines, alkyl amidopropyl betaines, alkyl amidopropyl hydroxysultaines, and mixtures thereof, wherein said surfactants contain C8 to C22 alkyl chains.

Nonionic synthetic surfactant cannot serve as the sole surfactant in this product, but can be used as a co-surfactant at a lower level of from about 1 parts to about 15 parts, by weight. The more preferred types selected from the group consisting: alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, EO/PO block co-polymers such as polyoxanines and poloxamers, sorbitan esters and alcohol esters, and mixtures thereof.

A preferred embodiment is liquid compositions containing from 0.5 parts to 8 parts C8–C14 soap; where the soap has a counterion selected from the group consisting of K and $N(CH_2CH_2OH)_3$, and mixtures thereof, in addition to the synthetic lathering surfactant.

Cationic synthetic surfactant cannot serve as the sole surfactant in this product, but are preferred as a co-surfactant at a lower level of from about 0.5 parts to about 6 parts, by weight. The more preferred types of cationic surfactants are selected from the group consisting: alkyl trimonium chloride and methosulfate, and dialkyldimonium chloride and methyl sulphate, and alkyl alkonium chloride and methyl sulphate and mixtures thereof. These surfactants contain C12 to C24 carbon atoms per alkyl chain. The most preferred cationic is selected from the group consisting of stearalkonium chloride, stearyltrimonium chloride, Di-stearyl-dimonium chloride, and mixtures thereof. Cationic surfactants may also act as a lipid deposition aid.

WATER AND THE AQUEOUS PHASE

The moisturizing and cleansing liquid compositions of the present invention comprise water as an essential component. The water is present at a level of from about 30 parts to about 80 parts, preferably from about 40 parts to about 75 parts, and most preferably from about 40 to about 65 parts. A substantial percentage of the water forms the key part of an aqueous phase, which may also contain other mater soluble components. Polyols and surfactants are water soluble.

While not being bound to any theory, the presence of a lipid in water emulsion is believed to be important to lipid deposition on the skin. The level of water is key to forming a lipid in water emulsion. Thus, an effective amount of water is required to form an aqueous phase to support the lipid in water emulsion. The level of aqueous phase to lipid is preferably greater than 2:1, more preferably greater than 3:1.

The upper range of water is adjusted to provide a desired liquid viscosity and liquid composition stability. Also enough water is required to properly process the liquid, so the lower amount of water is restricted by an ability to dispense the composition.

OPTIONAL INGREDIENTS

A highly preferred optional component of the present compositions are one or more humectants and solutes. A variety of humectants and solutes can be employed and can be present at a level of from about 0.5% to about 25%, more preferably from about 3.0% to about 20%, of a non-volatile, organic material having a solubility of a least 5 parts in 10 parts water. A preferred water soluble, organic material is selected from the group consisting of a polyol of the structure:

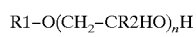

$$R1-O(CH_2-CR2HO)_nH$$

where R1=H, C1–C4 alkyl; R2=H, $CH_3$ and n=1–200; C2–C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D—, L—, and the D,L— forms); pyrrolidone carboxylic acid; hyaluronic acid; lactamide monoethanolamine; acetamide monoethanolamine; urea; and ethanol amines of the general structure $(HOCH_2CH_2)_xNH_y$ where x=1–3; y=0–2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Preferred water soluble organic material is preferred when elected from the group consisting of glycerine, polyoxypropylene (1) glycerol and polyoxypropylene (3) glycerol, sorbitol, butylene glycol, propylene glycol, sucrose, and urea and triethanolamine.

The use of oil thickening polymers, such as those listed in EP 0 547 897 A2 to Hewitt, published Jun. 23, 1993, incorporated herein by reference, are useful if the final rheology of lipid and polymer falls within the preferred range.

A preferred optional ingredient are one or more cationic and/or nonionic polymeric skin conditioning agents. A variety of polymers can be employed and can be present at a level of from about 0.1 parts to about 10 parts, and more preferably 0.25 parts to about 3 parts of a polymeric, nonionic, cationic or hydrophobically modified polymeric skin feel aid, selected from the group consisting of cationic polysaccharides of the cationic guar gum class with molecular weights of 1,000 to 3,000,000, cationic and nonionic homopolymers derived from acrylic and/or methacrylic acid, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines; and mixes thereof. Examples are hydroxypropyl guar, guar hydroxypropyltrimonium chloride, polyquaternary 3, 5, 6, 7, 10, 11 and 24. In order to achieve the benefits described in this invention, the polymer must have characteristics, either structural or physical which allow it to be suitably and fully hydrated and subsequently well incorporated into the soap matrix.

OTHER OPTIONAL COMPONENTS

A variety of additional ingredients can be incorporated into the compositions of the present invention. These materials including, but not limited to, liquid appearance aids, salts and their hydrates, clays, and other "filler materials" are listed in U.S. Pat. No. 5,340,492, to Kacher et al., issued Aug. 23, 1994, and U.S. Pat. No. 4,919,934, to Deckner et al., issued Apr. 24, 1990; which is incorporated herein by reference.

Other non limiting examples of these additional ingredients include vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

THE LIQUID COMPOSITION

As described above, the liquid dual composition of this invention can provide good cleansing and foaming and yet moisturize the skin via lipid deposition. The liquid composition of this invention itself has a Lipid Deposition Value (LDV) of at least 5 micrograms per sq. cm. This means that it will deposit at least 5 micrograms of lipid on a sq. cm of forearm skin using Lipid Deposition Protocol 1 disclosed herein.

While not being bound to any theory, the presence of an unstable lipid in water emulsion in the lather is believed to be key to deposition of lipid on the skin during the wash cycle.

The dual moisturizing and cleansing liquid of this invention can be made by either of the following processes:

SINGLE VESSEL PROCESS

1. Thickeners such as Carbopols, are added to a portion of the distilled water at room temperature and allowed to mix, hydrate for about 20 minutes or until mixture is thickened.
2. Distilled water, fatty acid flakes, Glycerin and Ethylene Glycol Distearate are heated together to 165–175 F. (73–80° C.).
3. If potassium soap is part of the composition, a caustic solution (45% active Potassium Hydroxide) is added and the mixture is stirred at a medium speed for 10–15 minutes until mixture is homogeous.
4. The synthetic surfactants are added (amphoteric, cationic and anionic) and temperature is allowed to cool by addition of ingredients to about 140 F. (60° C.), maintaining good mixing.
5. Polymer is added in one of several ways, depending on type. If the polymer is polyquaternium 10, it is premixed With one-half the amount of mineral oil or hydrogenated polybutene and added as a premix, mixed 5 minutes before continuing. Alternatively, Polyquaternium 10 is premixed with water and allowed to stir for 10–20 minutes to allow hydration of the polymer. If the polymer is polyox; it is added dry very slowly to the mix and allowed to stir until dispersed smoothly.
6. Any additional sensory aids such as silicones are added and allowed to mix 1–2 minutes.
7. A premix of lipid blend, (e.g. hydrogenated polybutene or mineral oil with petrolatum), at a temperature of 105–110° F. (40–43° C.), is added to the mixture at a temperature of 110–115° F. (43–46° C.) and allowed to stir for 2 minutes at a slow to medium setting. The duration and intensity of the mixing after lipid addition is considered important, especially with regards to particle size. Accordingly, if mixed too long or too fast, particle size and the resultant lipid deposition decreases.
8. The perfume is added and the batch is adjusted for water loss by weighing and back adding the amount lost due to evaporation during batch making.

THREE VESSEL PROCESS

1. A portion of the available surfactants (25–50%) is added to a portion of the available water (20%–50%), heated to 160° F. (71° C.), and agitated for about 20 minutes or until the surfactants are dissolved. Various (or multiples) types of surfactants (amphoteric, nonionic, cationic and anionic) are used in order to create a mixed surfactant system that maximizes Ethylene Glycol Distearate (EGDS) solubilization. The surfactant concentration is also important for this reason low water levels are used. However, high surfactant concentration negatively affects the crystallization of EGDS. Therefore a balance needs to be found between solubility and crystallization of EGDS. It is preferred to add surfactant in an order of addition according to the following: amphoteric, nonionic, anionic and cationic.
2. EGDS is added to the heated surfactant blend and allowed to dissolve and mix for about 20 to 30 minutes. Optical microscopy techniques are used to determine the time when maximum EGDS solubilization (approximately 60%) is achieved.
3. The EGDS dispersion is fast cooled using a plate and frame heat exchanger to a temperature of about 110° F. to 80° F. (43° C. to 27° C.) to form elongated EGDS crystals. The optimum freeze-out temperature is determined from the cooling curve of a DSC spectrum. Prior to passing through the heat exchanger, the temperature is maintained at 145–160° F. (63–71° C.) to reduce the formation of EGDS agglomerates that affect the quality of the EGDS crystals and reduce the stability of the final product.
4. In a separate vessel, the remaining water is used to dissolve and hydrate cationic polymers such as Polyquaternium 10, Merquat 550, or Jaguar. The polymer is added to cold water at medium to low agitation.
5. The solvent or any other water soluble organics such as Glycerine is added to the polymer solution to further dilute and thin the polymer solution.
6. Fatty acid flakes and Tetra Sodium EDTA are added and mixed for about 10 minutes and then heated to 160 to 170° F. (71 to 77° C.).
7. A caustic solution (45% active Potassium Hydroxide) is added and the mixture is agitated at a medium to high speed for 10–15 minutes until mixture is homogenous.
8. The temperature is reduced to about 120° F. (49° C.) with an in-line shell and tube heat exchanger. The remaining surfactants are added and the mixture.
9. When the temperature of the blend is between 110 to 90° F. (45 to 32° C.) the EGDS premix is added to this blend and allowed to mix for about 10 to 20 minutes.
10. Acrylates (e.g. Carbopol, Salcare) and cellulose (e.g. Bermocoll) type thickeners, sensory modifiers such as polyox, and perfumes are added and mix for about 10 minutes.

11. Any additional sensory aids such as silicones are added and allowed to mix 1–2 minutes.
12. A premix of lipid blend, either hydrogenated polabutene or mineral oil with petrolatum, at a temperature of 105–110° F. (40–44° C.), is mixed continuously with the surfactant/EGDS/Polymer mixture under controlled shear stress conditions (e.g. using a static mixer). The lipids premix can also be added to the mixture and mix in an agitated vessel as long as the applied shear and mix time are kept to a minimum. In both cases duration and intensity of the shear applied to the system considered important because both affect lipid deposition.

LIQUID HAND LATHER TEST

The hand wash lather test is used to provide in-use lather volume measurements for the lather performance of skin cleansing liquids. The test measures the lather volume generated under a soil load. Synthetic soil is used for the test reported herein. Its formula is reported in U.S. Pat. No. 4,673,525 to Small et al. issued Jun. 16th 1987, incorporated herein by reference.

The technician washes hands first with Ivory bar before starting test. The technician rubs 0.2 mls of synthetic soil into the dry palm of the hands. The technician then passes one hand through 95 F. city water, leaving a little water in palm of hand and dispenses 1.7 mls of test product into that hand. The technician then passes the other hand through the water and spreads product by rubbing palms together. The product is circulated on the palm and fingers of the hand 3 times then over the back of the hands once. This procedure is repeated continually 5 times. The technician gathers and scrapes the product off the hands and into a 250 ml beaker. A "flash" non soil volume grade is assigned based on the volume in the beaker. Alternatively, a lather grade is assigned to the amount and character of lather, based on a set of standards.

The same basic procedure is followed for "Ultimate" volume except that before the product is gathered and scraped into a beaker, an additional 2 mls of water is added to the hands and the product is again spread through the hands and circulated as outlined above continuously 5 more times, then the product is gathered/scraped into a 250 ml beaker and graded based on volume. Alternatively, a lather grade is assigned to the amount and character of lather, based on a set of standards.

THE EXAMPLES

Preferred Examples of Formulations Stabilized by Polymeric Gels

| Preferred Examples or Formulations Stabilized by Polymeric Gels | | |
|---|---|---|
| Ingredients | 1 | 2 |
| Sodium Laureth-3 Sulfate | 5.5 | 5.5 |
| Sodium C12/14 Alkyl Ether Glycerol Sulfonate | 5.5 | 5.5 |
| Sodium Lauroyl Sarcocinate | 2.0 | 2.0 |
| Cocoamidopropyl Betaine | 2.0 | 2.0 |
| Sodium Polyacrylate Copolymer | 1.5 | 2.0 |
| Polyquaternium 10 | 0.8 | 0.8 |
| Tallow Alcohol | 2.0 | 2.0 |
| Oleyl Alcohol | 1.0 | — |
| Myristic Acid | — | 2.0 |
| Petrolatum | 11.6 | 11.6 |
| Mineral Oil | — | — |
| Hydrogenated Polybutene | 2.9 | 2.9 |

-continued

| Preferred Examples or Formulations Stabilized by Polymeric Gels | | |
|---|---|---|
| Ingredients | 1 | 2 |
| Polyethylene Glycol (MW = 400,000) | 0.5 | 0.5 |
| Glycerine | 7.8 | 7.8 |
| perfume | 0.8 | 0.8 |
| Tetrasodium EDTA | 0.15 | 0.15 |
| DMDM Hydantoin | 0.4 | 0.4 |
| Water | 55.6 | 54.1 |
| Lather (Ultimate Soil Grade) | 4.5 | 4.5 |
| Deposition | 26 | 17 |
| Lipid in Water Emulsion Dilution Stability Test Clear Layer Separation (% of total sample) in 1 hour | 57% | 46% |

Preferred Examples 1 and 2 combine good lather, good deposition and stability. These products are stabilized and thickened by a combination of Sodium Polyacrylate Copolymer, Polyquaternium 10 and a mixture of tallow alcohol and oleyl alcohol for Example 1 and Tallow Alcohol and Myristic Acid for Example 2. These examples are the best formulations for lather and skin feel.

Examples of Formulations Stabilized by Various Polymeric Gels

| | Wt % | | | | |
|---|---|---|---|---|---|
| Ingredients | 3 | 4 | 5 | 6 | 7 |
| NaAE3S | 5 | 5 | 5 | 5 | 5 |
| Sodium Lauroyl Sarcosinate | 2 | 2 | 2 | 2 | 2 |
| Alkyl Ether Glyceryl Sulfate | 5 | 5 | 5 | 5 | 5 |
| Cocoamidopropyl Betaine | 2 | 2 | 2 | 2 | 2 |
| Polyquaternium 10 | .8 | .8 | .8 | .8 | .8 |
| Sodium Polyacrylate Copolymer | .5 | — | — | — | — |
| Hydroxy Ethyl Cellulose | — | .5 | — | — | — |
| Hydrophobically Modified Hydroxy Ethyl Cellulose | — | — | .5 | — | — |
| Hydroxyethylcellulose | — | — | — | .5 | — |
| Hydroxy Methyl Cellulose | — | — | — | — | .5 |
| Na$_2$EDTA | .14 | .14 | .14 | .14 | .14 |
| Fragrance | .8 | .8 | .8 | .8 | .8 |
| Petrolatum | .8 | .8 | .8 | .8 | .8 |
| Hydrogenated polybutene | 1.6 | 1.6 | 1.6 | 1.6 | 1.6 |
| Myristic Acid | 2 | 2 | 2 | 2 | 2 |
| Tallow Fatty Alcohol | 2 | 2 | 2 | 2 | 2 |
| Glycerin | 7.8 | 7.8 | 7.8 | 7.8 | 7.8 |
| DRO Water | QS | QS | QS | QS | QS |
| Viscosity | 17497 | 4915 | 4227 | 4718 | 2851 |

Examples 3, 4, 5, 6 and 7 have moderate deposition and lather and are stabilized by a variety of gel forming polymers. These Examples are stable.

Examples of Formulations Stabilized by Polymeric Gels

| | Wt % | |
|---|---|---|
| Ingredients | V | X |
| NaAE3S | 3 | 3 |
| Sodium Lauroyl Sarcosinate | 2 | 2 |
| AGS | 3 | 3 |
| Cocoamidopropyl Betaine | 2 | 2 |
| Cetyl Modified Hydroxy | — | .5 |

-continued

| Ingredients | Wt % | |
|---|---|---|
| | V | X |
| Ethyl Cellulose | | |
| Sodium Poyacrylate Copolymer | — | .5 |
| Stearyl Stearate | | 3.0 |
| PEG 600 | — | 3.0 |
| Polyquaternium 10 | .8 | .6 |
| Petrolatum | 10 | 10 |
| Mineral Oil | 2 | 2 |
| Glucam E20 Distearate | 1 | — |
| Myristis Acid | 2 | 2 |
| Tallow Fatty Alcohol | 2 | 2 |
| Citric Acid | | — |
| Fragrance | .8 | .8 |
| Na2EDTA | .14 | .14 |
| Preservative | .67 | .67 |
| Glycerin | 7.8 | 7.8 |
| DRO Water | QS | QS |
| Deposition | 20 | 30 |
| Viscosity | 11,000 cps | 6,000 cps |

Examples 8 and 9 demonstrate a skin feel benefit vs. a commercial benchmark, Oil of Olay Body Wash by being perceived by an expert panel as leaving skin feeling more moist.

What is claimed is:

1. A lathering skin cleansing liquid composition comprising by weight parts of the liquid composition:
   (a) from about 5 parts to about 30 parts of lipid skin moisturizing agent having a Vaughan Solubility Parameter (VSP) of between 5 and 10;
   (b) from about 0.3 parts to 5 parts of a water dispersible gel forming polymer wherein said polymer is an anionic, nonionic, cationic or hydrophobically modified polymers, selected from the group consisting of cationic polysaccharides of the cationic guar gum class with molecular weights of 1,000 to 3,000,000; anionic, cationic or nonionic homopolymers derived from acrylic or methylacrylic acid; anionic, cationic or nonionic cellulose resins; cationic copolymers of dimethyldialkylammonium chloride or acrylic acid; cationic homopolymers of dimethyldialkylammonium chloride; cationic polyalkylene or ethoxypolyalkylene imines; polyethylene glycol of molecular weight from 100,00 to 4,000,000; and mixtures thereof;
   (c) from about 5 part to about 30 parts of a synthetic surfactant;
   (d) from about 0 part to about 15 part of a C8 to C14 fatty acid soap; wherein said soap has a counterion selected from the group consisting of K, NH4, N(CH2CH2OH)3, and mixtures thereof; and
   (e) from about 0.5 parts to about 6 parts of an additional non-polymeric thickener selected from the group consisting of C10–C8 fatty alcohol and mixtures thereof;
   (f) water;
   wherein said lathering skin cleansing composition is a liquid,
   wherein said lathering skin cleansing liquid composition has a Lipid Deposition Value (LDV) of at least 5 up to about 1000;
   wherein said synthetic surfactant and said soap has a combined CMC equilibrium surface tension value of from 15 to 50; and
   wherein said composition is free of C10–C20 ethylene glycol fatty acid esters.

2. The lathering skin cleansing liquid composition of claim 1 wherein said water dispersible gel forming polymer is from about 0.8 parts to 3 parts and is selected from the group consisting of Sodium Polyacrylate, Hydroxy Ethyl Cellulose, Cetyl Hydroxy Ethyl Cellulose, and Polyquaternium 10; wherein said lipid skin moisturizing agent is from about 10 to 25 parts by weight of the composition; and wherein said lipid skin moisturizing agent is selected from the group consisting of hydrocarbon oils, hydrocarbon waxes, silicone oils, di-glyceride oils, tri-glyceride oils, acetoglyceride esters, polyol fatty acid polyesters, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol ricinolate, wax esters, vegetable waxes, sterols, phospholipids and mixtures thereof; wherein said lipid skin moisturizing agent has a Vaughan Solubility Parameter (VSP) of from about 5 to about 9 and a viscosity consistency k value of 5 poise to 5,000 poise at 35° C.; and wherein said lipid skin moisturizing agent has a shear index at 35° C. in the range 0.1 to 0.8; and wherein said liquid composition has a LDV (Lipid Deposition Value) of 10 to 400; and wherein said synthetic surfactant is from 5 to 25 parts; and wherein said synthetic surfactant has a critical micelle concentration (CMC) equilibrium surface tension value of from 25 to 40 dynes per cm at 25° C.; and said water is from about 30 parts to about 80 parts water.

3. The lathering skin liquid composition of claim 1 wherein said nonpolymeric thickener is from about 1.0 part to about 5 part and is selected from the group consisting of Cetyl Alcohol, Stearyl Alcohol, Oleyl Alcohol, and mixtures thereof.

4. The lathering skin cleansing liquid composition of claim 2 wherein said hydrocarbon oil or hydrocarbon wax is selected from the group consisting of petrolatum, mineral oil, micro-crystalline waxes, polyalkenes, paraffin, cerasin, ozokerite, polyethylene, perhydrosqualene and mixtures thereof; and said silicone oil is selected from the group consisting of dimethicones, cyclomethicones, alkyl siloxanes, polymetylsiloxanes and methylphenylpolysiloxanes; and said di and tri glycerides are selected from the group consisting of hydroxylated milk glyceride, castor oil, soy bean oil, maleated soy bean oil, safflower oil, cotton seed oil, corn oil, walnut oil, peanut oil, olive oil, cod liver oil, almond oil, avocado oil, palm oil and sesame oil; and said lanolin is selected from the group consisting of lanolin oil, lanolin wax, lanolin alcohol, lanolin fatty acid, isopropyl lanolate, acetylated lanolin, acetylated lanolin alcohols, lanolin alcohol linoleatel and lanolin alcohol riconoleate; and said wax esters is selected from the group consisting of beeswax, spermaceti, myristyl myristate and stearyl stearate; and said vegetable wax is selected from the group consisting of carnauba and candelilla waxes; and said sterol is selected from the group consisting of cholesterol and cholesterol fatty acid esters and said phospholipid is selected from the group consisting of lecithin, Sphingo lipids, ceramides, glycosphingo lipids and mixtures thereof; and wherein said hydrocarbon oil or wax is at least 50% of said lipid.

5. The lathering skin cleansing liquid composition of claim 4, wherein said liquid has a Lipid Deposition Value in the range 10 to 300; and wherein at least 70% of said lipid skin moisturizing agent is selected from the group consisting oil petrolatum, mineral oil, micro-crystalline wax, polyalkene, paraffin, cerasin, ozokerite, polyethylene, perhydrosqualene, dimethicones, alkyl siloxane, polymethylsiloxane, methylphenylpolysiloxane and mixtures thereof and wherein said lipid skin moisturizing agent has a shear index at 35° C. in the range 0.1 to 0.5 and a consistency k at 35° C. in the range 10 to 3,000 poise; and wherein at least 70% of said lipid skin moisturizing agent has a Vaughan Solubility Parameter (VSP) of from about 6.5 to about 7.75 ; and said water is from about 40 to 70 parts of said composition.

6. The lathering skin cleansing liquid composition of claim 5, wherein said lipid skin moisturizing agent is from about 10 parts to about 25 parts, by weight of the liquid composition; and wherein said lipid skin moisturizing agent has a k value of 50 to 2000 poise; and wherein at least 75% of said lipid skin moisturizing agent is selected from the group consisting of petrolatum, mineral oil, hydrogenated polybutene, polydecene, and mixtures thereof, and wherein of said petrolatum to said hydrogenated polybutene or polydecene or mineral oil have a ratio of from about 10:1 to about 1:3; and wherein from about 0% to about 25% of said lipid skin moisturizing agent is said silicone oil and wherein said lipid skin moisturizing agent has an elastic modulus (G') measured at 1 Hz. and 35° C. in the range 1,000 to 80,000 dynes/sq. cm and has a viscous modulus (G") measured at 1 Hz. and 35°° C. in the range 500 to 300,000 dynes/ sq. cm.

7. The lathering skin cleansing liquid composition of claim 6, wherein the ratio of said petrolatum to said hydrogenated polybutene or polydecene or mineral oil is from about 5:1 to about 1:1.

8. The lathering skin cleansing liquid composition of claim 1 wherein said water is present at a higher level than said lipid; and wherein said water level is from 40 to 75 parts; and wherein said water and said lipid skin moisturizing agent form a lipid in water emulsion; and wherein said emulsion is shelf stable, but is an unstable lipid in water emulsion when subjected to the Lipid Release Test.

9. The lathering skin cleansing liquid composition of claim 2 wherein said synthetic surfactant parts is from about 5 to about 25 parts, and wherein said synthetic surfactant comprises anionic surfactants and mixtures of anionic surfactants with surfactants selected from the group consisting of amphoteric surfactants, nonionic surfactants, cationic surfactants and mixtures thereof.

10. The skin cleansing liquid composition of claim 9, wherein said composition contains from 0.5 parts to 8 parts C8–C14 soap; said soap having a counterion selected from the group consisting of K, N(CH2CH2OH)3, and mixtures thereof.

11. The lathering skin cleansing liquid composition of claim 1 wherein said synthetic surfactant includes from about 1 part to about 10 parts of an amphoteric surfactant selected from the group consisting of alkyl-ampho monoacetates or alkyl-ampho di-acetates, alkyl dimethyl amine oxides, alkyl betaines, alkyl sultaines, alkyl amidopropyl betaines, alkyl amidopropyl hydroxysultaines, and mixtures thereof, wherein said amphoteric surfactant have C8 to C22 alkyl chains.

12. The lathering skin cleansing liquid composition of claim 2 wherein said synthetic surfactant comprises from about 1 part to about 15 parts of a nonionic lathering synthetic surfactant selected from the group consisting of alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, EO/PO block co-polymers, sorbitan esters, alcohol esters, and mixtures thereof.

13. The lathering skin cleansing liquid composition of claim 1 wherein said composition contains from about 0.5 to about 25 parts water soluble, organic material and wherein said water soluble organic material is selected from the group consisting of a polyol of the structure:

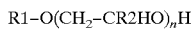

where R1=H, C1–C4 alkyl R2=H, $CH_3$ and n=1–200, C2–C10 alkane diols, guanidine, glycolic acid, glycolate salts, lactic acid, lactate salts, polyhydroxy alcohols, polyethylene glycol, sugars, starches; D-panthenol, L-panthenol, D,L-panthenol, pyrrolidone carboxylic acid, hyaluronic acid, lactamide monoethanolamine, acetamide monoethanolamine, urea, ethanol amines of the general structure $(HOCH_2CH_2)_xNH_y$ where x=1–3; y=0–2, and x+y=3, and mixtures thereof; and wherein said water soluble organic material at least 50% soluble in water.

14. The lathering skin cleansing liquid composition of claim 2 wherein said polymer is from about 0.25 parts to about 3 parts by weight selected from the group consisting of polyethylene glycol, hydroxypropyl guar, guar hydroxypropyltrimonium chloride, polyquaternary 3, 5, 6, 7, 10, 11 or 24 and mixtures thereof.

15. The lathering skin cleansing liquid composition of claim 1, wherein said lipid skin moisturizing agent has an elastic modulus (G') measured at 1Hz and 35° C. in the range 25 to 100,000 dynes/sq. cm and has an viscous modulus (G") measured at 1Hz and 35° C. in the range 25 to 500,000 dynes/sq.

16. The lathering skin cleansing liquid composition of claim 13 wherein said elastic modulus (G') is in the range of 5,000 to 50,000 dynes/sq. cm and has a viscous modulus (G") in the range of 5,000 to 100,000 dynes/sq.cm.

17. The lathering skin cleansing liquid composition of claim 2 wherein said water dispersible gel forming polymer is from about 2 parts to 3 parts; and wherein said water dispersible gel forming polymer is selected from the group consisting of from 1 part to 2.5 parts Sodium Polyacrylate and from 0.5 parts to 1.0 parts Polyquaternium 10; and wherein said lipid skin moisturizing agent is from about 13 to 18 parts; and wherein said lipid skin moisturizing agent is selected from the group consisting of 1 petrolatum and hydrogenated polybutene and wherein the ratio of said petrolatum to polybutene is from 3:1 to 5:1; and wherein said liquid composition contains from 2 parts to 5 parts of a thickener selected from the group consisting of tallow fatty alcohol, oleyl fatty alcohol, and wherein said synthetic surfactant is from 12 to 20 parts; and wherein said synthetic surfactant is selected from the group consisting of from 3 parts to 8 parts Sodium Laureth-3 Sulfate, from 3 parts to 8 parts Sodium C12/14 Alkyl Ether Glycerol Sulfonate, from 0.5 parts to 4 parts Sodium Lauroyl Sarcosinate, and from 0.5 parts to 4 parts Cocoamidopropyl Betaine; and said water level is from about 50 parts to about 60 parts; and wherein said liquid composition contains from 4 parts to 12 parts glycerin.

* * * * *

UNITED STATES PATENT AND TRADEMARK OFFICE
CERTIFICATE OF CORRECTION

PATENT NO. : 6,033,680
DATED : March 7, 2000
INVENTOR(S) : Dixon et al.

It is certified that error appears in the above-identified patent and that said Letters Patent is hereby corrected as shown below:

Column 19,
Line 45, "100,00" should read -- 100,000 --.

Column 20,
Line 49, "linoleatel" should read -- linoleate, --.

Column 22,
Line 11, "C1-C4 alkyl" should read -- C1-C4 alkyl; --.
Line 34, "claim 13" should read -- claim 18 --.
Line 45, "of 1" should read -- of --.

Signed and Sealed this

Fifth Day of March, 2002

Attest:

JAMES E. ROGAN
Attesting Officer  Director of the United States Patent and Trademark Office